US005185029A

United States Patent [19]

Norris

[11] Patent Number: 5,185,029

[45] Date of Patent: Feb. 9, 1993

[54] METHOD FOR INDUCING RESISTANCE IN PLANTS USING ENVIRONMENTALLY SAFE ANTIOXIDANTS

[76] Inventor: Dale M. Norris, 101 S. Rock Rd., Madison, Wis. 53705

[21] Appl. No.: 678,074

[22] Filed: Apr. 1, 1991

Related U.S. Application Data

[63] Continuation of Ser. No. 205,157, Jun. 10, 1988, Pat. No. 5,004,493.

[51] Int. Cl.$^5$ .............................................. A01N 37/44

[52] U.S. Cl. ...................................................... 504/320

[58] Field of Search ............................ 71/98, 106, 113

[56] References Cited

PUBLICATIONS

Freebairn et al., *American Society for Horticultural Science,* vol. 76 (1960), pp. 693-699.

Arrigoni et al., *Chem. Abst.*, vol. 91 (1979), 154424.

J. P. 82 134 405, *Chem. Abst.*, vol. 97 (1982), 210482 D.

Khanna et al., *Chem. Abst.*, vol. 87 (1977) 180967.

*Primary Examiner*—Richard L. Raymond

*Attorney, Agent, or Firm*—Stroud, Stroud, Willink, Thompson & Howard

[57] ABSTRACT

The present invention describes a method for increasing the resistance of plants to pests or pathogens by administering to the surface of the plant environmentally safe antioxidants such as ascorbates, tocopherals, reduced glutathione and its derivatives, and cysteines (half cystines). The administration to a portion of the surface of the plant of an effective amount of such environmentally safe antioxidants induces in the plant a protective response which is systemic in nature. Application may be made by a variety of ways including drenching the root system of the plant, spraying the plant with a solution containing an effective amount of antioxidant, or direct application to the stem of the plant with the antioxidant contained in a suitable carrier.

2 Claims, No Drawings

METHOD FOR INDUCING RESISTANCE IN PLANTS USING ENVIRONMENTALLY SAFE ANTIOXIDANTS

This is a continuation of copending application Ser. No. 07/205,157, filed Jun. 10, 1988, now U.S. Pat. No. 5,004,493.

FIELD OF THE INVENTION

This invention relates to the general subject matter of plant pest and pathogen control and, in particular, to a method of causing plants to become more resistant to environmental stresses by the application of environmentally safe antioxidants.

BACKGROUND OF THE INVENTION

Plants, like any living organism are subjected to numerous environmental stresses which are both biotic and abiotic. Biotic stresses include pests such as insects, arachnids, and nematodes, and pathogens such as bacteria, viruses and mycoplasms. Abiotic stresses would include drought and extremes in temperature. Each year these stresses result in billions of dollars worth of loss as a result of damaged or diminished crop production. Thus, control of the effects of such stresses on valued plants is one of man's major concerns.

Since 1945, control efforts to protect plants against such stress factors have utilized principally synthetic toxic chemicals (pesticides). Annual usage of pesticides has increased to over 544 million kilograms. Pesticides, however, are expensive to bring to market and consequently expensive to use. Furthermore, because of their persistance in the environment, they present a continually growing health risk to animal and human life.

The economic and health risk cost of pesticide use has led to an ever-increasing emphasis on alternative strategies of plant protection. One such alternative strategy has been to search for methods to enhance the plants own defense mechanisms.

It has been known for some time that certain stressful stimuli will increase a plant's resistance to pathogens. In 1940, Muller and Borges discovered phytoalexins. Muller, K. O. and Borges, H. Arb. Biol. Reichsanst Land-u Forstwiss. 23 189-231 (1940). The discovery of phytoalexins provided the biochemical explanation for what had been observed to be an inducible defense response. Subsequently, it has been shown that exposure to a variety of biotic or abiotic stresses (exo-elicitors) will cause the plant to synthesize and accumulate phytoalexins. These phytoalexins display antifeedant and antibiotic properties which are protective to the plant. They have been shown to be toxic to fungi, bacteria, higher-plant cells, and also animal cells. J. Ebel, *Phytoalexin Synthesis: The Biochemical Analysis of the Inductive Process,* 24 Ann. Rev. Phytopathol, 235-64, 1986. These exo-elicitors may also induce other chemical defense mechanisms besides phytoalexins, e.g., protease inhibitors and hormone mimics.

Biotic exo-elicitors which have been studied to date include: *Phytophthora megasperma* var. sojae (a fungus) (Klarman, W. L. Netherlands Jour. Plant Pathol. 74: 171-175 (1968); Chamberlain, D. W. and J. D. Paxton, Phytopathology 58: 1349-1350, (1968); *Meloidogyne incognita* (a nematode) (Kaplan, D. T., N. T. Keen and I. J. Thomason. Physiol Plant Pathol. 16: 309-318, 1980); *Pseudomonas syringae* pv. glycinea (a bacterium) (Holliday, M. J., N. T. Keen and M. Long. Physiol. Plant Pathol. 18: 279-287, 981); several species of insects (Kogan, M., and J. Paxton, in: P. A. Hedin (ed.), Plant Resistance to Insects, Amer. Chem. Soc., Wash., D.C. 1983); *Tetranychus urticae* (a mite) (Hildebrand, D. F., J. G. Rodriguez, G. C. Brown, K. T. Luu and C. S. Volden. Jour. Econ. Entomol. 79: 1459-1465, 1986); and *Epilachna varivestis* (an insect) (Chiang, H. S., D. M. Norris, A. Ciepiela, P. Shapiro and A. Oosterwyk. Jour. Chem. Ecol. 13: 741-749, 1987).

Although such biotic exo-elicitors have been shown experimentally to increase plant resistance, they may be themselves pests or pathogens of plants. Further, large scale production of biotic exo-elicitors that display uniform activity in a quantity necessary for practical use would be difficult and costly under the best of circumstances. Thus, at present, biotic exo-elicitors do not appear to be a satisfactory alternative to toxic pesticides.

Abiotic exo-elicitors have been identified among: fungicides and fungicidal decomposition products (Reilly, J. J. and W. L. Klarman. Phytopathology 62: 1113-1115, 1972); maneb, ethylenediamine, polyethylene (thiocarbamoyl) monosulfide (PTM) and benomyl are representative of such fungicides; ultraviolet irradiation was active in soybean (Bridge, M. A. and W. L. Klarman. Phytopathology 63: 606-609, 1973); mercuric chloride (Moesta, P., and H. Grisebach. Nature 286: 710-711, 1980); acifluorfen and oxyfluorfen herbicides (Komives, T., and J. E. Casida. Jour. Agric. Food Chem. 31: 751-755, 1983); dithiothreitol (DTT), N-ethylmaleimide (NEM), p-hydroxymercuribenzoate (PHMB) and p-chloromercuribenzenesulfonic acid (PMBS) (Stoessel, P. Planta 160: 314-319, 1984); and a glucan molecule (Grisebach, H., H. Boerner, M. L. Hagman, M. G. Hahn, J. Leube and P. Moesta. UCLA Symp. Mol. Cell Biol., Ser. 22: 275-290, 1985).

Unfortunately, these experimental abiotic exo-elicitors persist in the environment and are toxic to living organisms—both plant and animal. Thus, while useful for study, they do not avoid the problems already presented by the toxic pesticides.

SUMMARY OF THE INVENTION

The present invention avoids the problems existent with use of toxic pesticides while at the same time achieving significant practical pest and pathogen control. More specifically, the present invention describes a heretofore unknown class of exo-elicitors which are biodegradable, non-pesticidal, non-toxic and environmentally compatible antioxidants. Included within this class of environmentally safe antioxidants are ascorbates, tocopherols, reduced glutathione and its derivatives, and cysteines (half cystines). The term ascorbates is intended to include all forms, isomers and derivatives of ascorbic acid (including Vitamin "C" or L-ascorbic acid) which have antioxidant and reducing power. The term tocopherol is intended to include Vitamin "E" (2, 5, 7, 8-tetramethy-2-(4′, 8′, 12′-trimethyltridocyl)-6-chromanol), all isomers of tocopherol which have antioxidant or reducing power and all tocopherol esters and other derivatives which have antioxidant or reducing power. Application to the surface of a plant of an effective amount of one or more of such environmentally safe antioxidants elicits a protective response in the plant. The defensive response thus elicited is systemic in nature. Thus, treatment of one portion of a plant elicits a defensive response throughout the plant. The effectiveness of the exo-elicitors, herein described, to elicit a defensive response is facilitated by administering such exo-elicitors dispersed in a non-reactant, membrane permeable, carrier.

Accordingly, it is one object of the present invention, to provide a method for plant pest and pathogen control which utilizes environmentally safe, yet effective, compositions for the treatment of plants.

It is another object of the present invention to provide a method for plant pest and pathogen control which utilizes compositions for the treatment of plants which are easy and economical to manufacture and use.

EXAMPLE 1

Sweet corn, bush beans, broccoli, and geranium were treated with ascorbic acid (Vitamin "C") as a 10-5M solution in water. Control plants treated with water alone were also studied. Treatment was accomplished by a single spray of the entire above-ground plant surface so as to thoroughly wet it to the run-off point. At preselected times (72, 96, 120 and 168 hours) after treatment, randomly chosen leaves were selected from each plant (treatment or control); and standardized discs cut from each leaf were bioassayed to measure the degree of inducible protective response. The bioassay consisted of giving one 4th-instar larva of *T. ni* or *Q. nubilalis* a choice of feeding on a standardized leaf disc from the treated versus the control ($H_2O$-treated) plant in a two-choice petri-dish arena under standardized environmental conditions in 24 hours or less. See Chiang, H. S. et al., Jour. Chem. Ecol. 13 : 741–49 (1987). There were at least 15 replicate assays per treatment or control. Area eaten per disc is measured in cm2 using an electronic area meter. Results of such an experiment are given in Table 1.

TABLE 1

Comparative feeding ($cm^2$) of a *Trichoplusia ni* or *Ostrinia nubilalis* larva on a leaf disc from a stressed (treated with ascorbic acid in $H_2O$ spray) versus an unstressed ($H_2O$ sprayed control) plant-broccoli, geranium, sweet corn or bush bean-in a two-choice bioassay.[1]

| Plant | Treatment | Area eaten ($cm^2$) ($\bar{X} \pm$ S.E.) 0.475 indicated hous after treatment[2] 72 hr | replicates, hr | 120 hr | 168 hr |
|---|---|---|---|---|---|
| Broccoli | Ascorbic acid ($10^{-5}$ M) in $H_2O$ spray (A) | $0.322 \pm 0.05^a$ | $0.305 \pm 0.07^a$ | $0.211 \pm 0.05^{a**}$ | $0.294 \pm 0.06^a$ |
| | $H_2O$ spray (control) (C) | $0.285 \pm 0.06^a$ | $0.215 \pm 0.04^a$ | $0.553 \pm 0.07^b$ | $0.423 \pm 0.07^a$ |
| Geranium | A | $0.301 \pm 0.08^a$ | $0.342 \pm 0.07^a$ | $0.642 \pm 0.12^a$ | |
| | C | $0.233 \pm 0.08^a$ | $0.233 \pm 0.06^a$ | $0.553 \pm 0.12^a$ | |
| Bush bean | A | $0.346 \pm 0.07^a$ | $0.215 \pm 0.06^a$ | $0.203 \pm 0.06^{a*}$ | $0.274 \pm 0.07^{a*}$ |
| | C | $0.244 \pm 0.06^a$ | $0.130 \pm 0.04^a$ | $0.380 \pm 0.06^b$ | $0.507 \pm 0.6^b$ |
| Corn[3] | A | $0.208 \pm 0.06^a$ | | $0.164 \pm 0.06^{a**}$ | |
| | C | $0.234 \pm 0.06^a$ | | $.475 \pm 0.07^b$ | |

[1]Mean value based on 20 replactes, except for 15 replicates with corn.
[2]In each column, pairs of values followed by the same letter are not significantly different (*$P < 0.05$, **$P < 0.01$) based on the Student 't' test.
[3]The bioassay insect was *Ostrinia nubilalis.*

These results clearly show that treatment of the plants as described in this example produces a long-lasting, protective response.

EXAMPLE 2

In another experiment, the procedures were as in EXAMPLE 1 except the treatment was a combination of ascorbic acid (5×10-6M)+Vitamin "E" (200 IU/liter) in a water spray. Results are given in Table 2.

TABLE 2

Comparative feeding ($cm^2$) of a *Trichoplusia ni* or *Ostrinia nubilalis* larva on a leaf disc from a stressed (treated with ascorbic acid + Vitamin "E" in $H_2O$ spray) versus unstressed ($H_2O$ sprayed control) plants-broccoli, geranium, sweet corn or bush bean-in a two-choice bioassay.[1]

| Plant | Treatment | Area eaten ($cm^2$) ($\bar{X} \pm$ S.E.) at indicated hours after treatment[2] 72 hr | 96 hr | 120 hr | 168 hr |
|---|---|---|---|---|---|
| Broccoli | Ascorbic acid ($5 \times 10^{-6}$ M) + Vitamin "E" (200 IU/l) in $H_2O$ spray (B) | $0.209 \pm 0.05^a$ | $0.174 \pm 0.04^{a*}$ | $0.150 \pm 0.05^{a**}$ | $0.313 \pm 0.07^{a*}$ |
| | $H_2O$ spray (control) (C) | $0.313 \pm 0.05^a$ | $0.325 \pm 0.05^b$ | $0.367 \pm 0.05^b$ | $0.510 \pm 0.07^b$ |
| Geranium | B | $0.258 \pm 0.08^a$ | $0.271 \pm 0.06^a$ | $0.360 \pm 0.11^a$ | |
| | C | $0.348 \pm 0.10^a$ | $0.180 \pm 0.024^a$ | $0.574 \pm 0.12^a$ | |
| Bush bean | B | $0.424 \pm 0.07^a$ | $0.145 \pm 0.03^{a*}$ | $0.273 \pm 0.06^{a*}$ | $0.369 \pm 0.07^{a*}$ |
| | C | $0.266 \pm 0.05^a$ | $0.322 \pm 0.07^b$ | $0.419 \pm 0.06^b$ | $0.415 \pm 0.05^b$ |
| Corn[3] | B | $0.335 \pm 0.08^a$ | | $0.167 \pm 0.03^{a**}$ | |
| | C | $0.453 \pm 0.07^a$ | | $0.405 \pm 0.06^b$ | |

[1]Mean value based on 20 replicates, except for 15 replicates with corn.
[2]See footnote 2, Table 1.
[3]The bioassay insect was *Ostrinia nubilalis.*

The results clearly show that treatment of the plants with a combination of Vitamins "C" and "E", as described in this example, produces a protective response having a better residual effectiveness than is observed with treatment with Vitamin "C", alone.

Examples 1 and 2, above, used the method of application of spraying so as to thoroughly wet to the run-off point the above ground surface of the plant with a solution of exo-elicitor in water. Application may also be made by drenching the root system or soaking the seeds. The use of an aqueous solution of exo-elicitor should not be construed as excluding the use of other solvents. Any non-phytotoxic, non-reactant agent in which the anti-oxidants can be diluted or dispersed will suffice and are considered to fall within the scope of the claims. In fact, as demonstrated in Example 3, below, those diluents which adhere to a given plant surface, are non-reactant, membrane permeable and guard the exo-elicitor against oxidation tend to enhance the ability of the elicitor to induce a protective response.

The above examples 1 and 2 should also not be construed as limiting the concentration of spray to a narrow range. Effectiveness can be expected at concentrations between 10-6 and 10-4 Molar.

EXAMPLE 3

In another study, two treatment levels of vitamin "E" (25 and 50 IU) where applied in 1 milliliter of paraffin (white) oil in a 1-cm wide bandaid wrapped around the base of the stem of each coleus plant. The control treatment was 1 milliliter of paraffin oil in the bandaid. Assay intervals were 72, 120, 168 and 224 hours. Other aspects of the experiment where as described above. Results are presented in Table 3.

TABLE 3

Comparative feeding ($cm^2$) of a *Trichoplusia ni* larva on a leaf disc from stressed (Vitamin "E" - treated) versus unstressed (no Vitamin "E" treatment) Coleus plants in a two-choice bioassay.[1]

| | Area eaten ($cm^2$) (mean ± S.E.) at indicated hour after treatment[2] | | | |
|---|---|---|---|---|
| Treatment | 72 hr | 120 hr | 168 hr | 224 hr |
| Vitamin "E" (25 IU) | 0.201 ± 0.04[a**] | 0.219 ± 0.04[a**] | 0.170 ± 0.04[a**] | 0.577 ± 0.10[a] |
| Control (white oil[3]) | 0.492 ± 0.06[b] | 0.543 ± 0.07[b] | 0.634 ± 0.08[b] | 0.592 ± 0.08[a] |
| Vitamin "E" (50 IU) | 0.161 ± 0.03[a**] | 0.167 ± 0.04[a**] | 0.204 ± 0.06[a**] | 0.563 ± 0.07[a] |
| Control (white oil) | 0.513 ± 0.04[b] | 0.453 ± 0.05[b] | 0.496 ± 0.05[b] | 0.572 ± 0.09[a] |

[1]Each mean is based on 20 replicate bioassays.
[2]See footnote 2, Table 1.
[3]White oil is also called paraffin oil.

These results clearly demonstrate the systemic nature of the protective response. When compared with Example 2, the results also indicate that the protective response is enhanced in magnitude and duration if the exo-elicitor is dispersed in a non-reactant, membrane permeable carrier such as a heavy mineral oil. Examples 3 and 4 used paraffin oil as the carrier, however, other types of oils such as white oil or liquid petrolatum should be considered to fall within the scope of the claims. Regardless of the specific type of carrier, caution should be taken to assure that the carrier contains no stabilizers or other materials which may react with the antioxidant.

EXAMPLE 4

Treatment of Fraxinus spp. (ash), Quercus spp. (oaks) and *Gleditsia triacanthos* L. (honey locust) trees, which have a trunk circumference of 10 centimeters (cm) at 35 cm above the ground surface and a height of 4 meters, with a 10×8.3-cm trunk-banding gauze bandage bearing 0.5 ml of paraffin oil per $cm^2$ containing 25-50 IU (international units) of Vitamin "E" elicitor per ml, can be expected to significantly ($P<0.05$ or better) reduce the amount of leaf area ($cm^2$) eaten by assay insects, *Malacosoma disstria* Hubner (the forest tent caterpillar) or *Lymantria dispar* L. (the gypsy moth larva), as compared to that eaten on control (non-stressed) trees. Residual effectiveness of the elicitor can be expected to be 4-14 days per treatment. This effectiveness is comparable to that yielded by commercial toxic pesticides.

In examples 3 and 4, the exo-elicitor is applied to the plant via a stem bandage. In using this method, the following procedure for determining dosage is recommended:

a. Determine the stem circumference in centimeters (cm).

b. Determine the application rate (AR) for the exo-elicitor.

The accompanying graph describes the minimal and maximal recommended application rates in international units (IU) of antioxidant (e.g., Vitamin "E") per plant.

MINIMAL AND MAXIMAL RECOMMENDED ELICITOR APPLICATION RATES (IU/PLANT) VS. CIRCUMFERENCE IN CM.

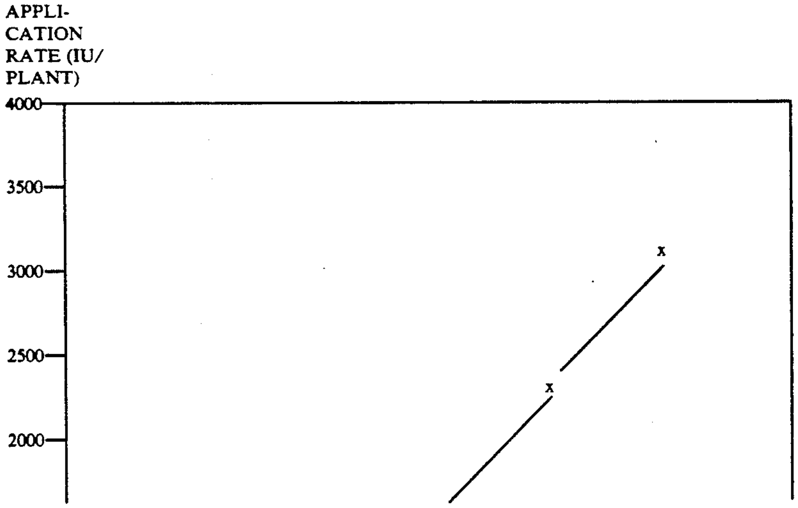

-continued

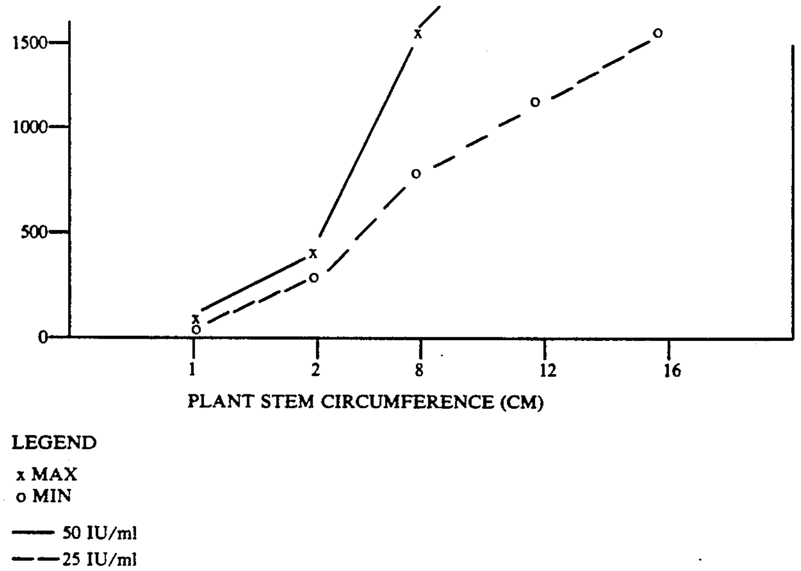

Example: With a 10 cm stem circumference, the maximal recommended application rate (AR) is 2080 IU/plant at 50 IU/ml of diluent, and the minimal recommended application rate (AR) is 1040 IU/plant at 25 IU/ml of diluent.

c. Determine the application volume (AV) for the exo-elicitor.

Divide the application rate (AR) (see (6), above) by the concentration (C) (i.e., IU/ml) to determine the application volume (AV).

Example: At AR=2080 IU/plant and C=50 IU/ml, the application volume (AV)=2080 IU per plant/50 IU per ml=41.6 ml/plant. At AR=1040 IU/plant and C=25 IU/ml, the application volume (AV)=1040 IU per plant/25 IU per ml=41.6 ml/plant.

d. Determine the application surface (AS).

The stem bandage used in examples 3 and 4 is a gauze-bandage. That is a rectangle of gauze which is wrapped around the stem. Assuming this gauze rectangle saturates with the particular diluent or carrier used at a concentration of 0.50 ml carrier/cm2, then the application surface (AS) is determined by dividing the application volume (AV) (see (c), above) by 0.50 ml/cm2.

Example: At AV=41.6 ml/plant the application surface (AS)=41.6 ml per plant/0.50 ml per cm2=83.2 cm2/plant.

e. Determine the rectangle size for the gauze-bandage dressing.

In order to determine the size of the gauze rectangle required in order to encircle the stem, divide the application surface (AS) (see (d), above) by the stem circumference of the plant. The resultant number is one dimension of the application rectangle (AR) of the dressing. The other dimension of the application rectangle (AR) is the stem circumference.

Example: For an application surface (AS) of 83.2 cm2/plant and a circumference of 10 cm, the application rectangle (AR) is 10 cm by 83.2 cm2/10 cm=8.3 cm; 10×8.3 cm.

f. Procedure for Application to the Plant.

Pour the application volume (AV) evenly over the determined application surface (AS) of the gauze-bandage dressing. Place the prepared bandage around the plant, make it snug around the stem and then staple together the ends to secure the bandage in place. Cover the in-place bandage with a slightly larger piece of white 1-mil plastic, make it snug around the stem and staple it in place.

The use of paraffin oil as a diluent should not be construed as excluding other carriers. Paraffin oil serves nicely because it is non-phytotoxic, non-reactive, protects the exo-elicitors from oxidation and is adhesive to the plant surface. Any carrier meeting these criteria should be considered to fall within the scope of the claims of this invention.

Also considered to fall within the scope of the claims of this invention is the use of the exo-elicitors described herein in combination with other agricultural chemicals, including pesticides. Such combined use would permit less toxic levels of pesticides to be used while still maintaining a satisfactory level of pesticide protection.

What I claim is:

1. A method for increasing the resistance of a plant to pests or pathogens comprising the step of administering to the surface of said plant an amount of one or more environmentally safe antioxidants effective to induce said resistance, said environmentally safe antioxidants being reduced glutathiones and cysteines.

2. A method for increasing the resistance of plants to pests or pathogens comprising the step of spraying the above ground surface of the plant with a solution containing an amount of one or more environmentally safe antioxidants effective to induce said resistance, said environmentally safe antioxidants being reduced glutathiones and cysteines.

* * * * *